United States Patent
Jung

(10) Patent No.: US 7,205,332 B2
(45) Date of Patent: Apr. 17, 2007

(54) DEOXOARTEMISININ ANALOGS, PROCESS FOR THEIR PREPARATION, AND ANTICANCER AGENT COMPRISING THEM

(75) Inventor: Man-Kil Jung, Seoul (KR)

(73) Assignee: Industry-Academic Cooperation Foundation, Yonsei University, Seoul (KR)

( * ) Notice: Subject to any disclaimer, the term of this patent is extended or adjusted under 35 U.S.C. 154(b) by 0 days.

(21) Appl. No.: 10/543,117

(22) PCT Filed: Jan. 19, 2004

(86) PCT No.: PCT/KR2004/000086

§ 371 (c)(1),
(2), (4) Date: Jul. 22, 2005

(87) PCT Pub. No.: WO2004/078762

PCT Pub. Date: Sep. 16, 2004

(65) Prior Publication Data

US 2006/0074251 A1    Apr. 6, 2006

(30) Foreign Application Priority Data

Jan. 23, 2003   (KR) .................. 10-2003-0004511

(51) Int. Cl.
*A61K 31/35* (2006.01)

(52) U.S. Cl. ................. 514/450; 549/346; 549/354
(58) Field of Classification Search ............. 514/450; 549/346, 354

See application file for complete search history.

(56) References Cited

FOREIGN PATENT DOCUMENTS

WO    WO 93/08195    4/1993

OTHER PUBLICATIONS

Jung, M et al, Antitumor Activity of Novel Deoxoartemisinin Monomers, Dimers, and Trimer, J. Med. Chem. 2003, 46, 987-994.*
Efferth, T, Mechanistic perspectives for 1,2,4-trioxanes in anticancer thereapy, Drug Resistance Updates 8 (2005) 85-97.*
1st Citation in ISR, 1993, Ognyanov et al.
2nd Citation in ISR, Mar. 13, 2003, Jung et al.

* cited by examiner

*Primary Examiner*—Amelia A. Owens
(74) *Attorney, Agent, or Firm*—IPLA P.A; James E. Bame

(57) ABSTRACT

The present invention relates to a new deoxoartemisinin dimer and trimer, which have excellent anticancer activity and lower toxicity and are stable to acids, to a new deoxoartemisinin monomer of intermediate thereof, to preparations thereof, and to anticancer agents comprising the deoxoartemisinin dimer or trimer.

4 Claims, No Drawings

DEOXOARTEMISININ ANALOGS, PROCESS FOR THEIR PREPARATION, AND ANTICANCER AGENT COMPRISING THEM

TECHNICAL FIELD

The invention relates to deoxoartemisinin analogs, process for their preparation and anticancer agent comprising them. More particularly, the present invention relates to a new deoxoartemisinin dimer and trimer, which have excellent anticancer activity and lower toxicity and are acid stable, to a new deoxoartemisinin monomer of intermediate thereof, to preparations thereof, and to anticancer agents comprising the deoxoartemisinin dimer or trimer.

BACKGROUND ART

Artemisinin (Qinghaosu)(I), a sesquiterpene lactone endoperoxide, is the first natural trioxane isolated from *Artermisia annua*, L.

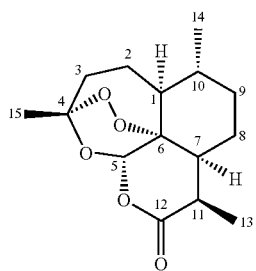
I

The artemisinin is of special biological interest because of its outstanding antimalarial activity and outstanding activity against *pneumocystis carinii* and *toxoplasma gondii*. The anti-human immunodeficiency virus (HIV) activity of artemisinin derivatives has been also reported. Artemisinin has been subjected to a number of reviews because of its novel structure and outstanding antimalarial activity. Most first generation C-12 acetal type derivatives are hydrolytically unstable. Also, most semi-syntheses have involved replacing the C-12 acetal functionality in ether derivatives by less hydrolytically prone functional groups. Recently, however, C-12 non-acetal-type deoxoartemisinin (III) prepared from either artemisinin of formula (I) or artemisinic acid of formula (II) has been reported to show more antimalarial activity than that of artemisinin both in vitro and in vivo (see Jung, M.; Li, X.; Bustos, D. A.; ElSohly, H. N.; McChesney, J. D., A Short and Stereospecific Synthesis of (+)-Deoxoartemisinin and (−)-Deoxodesoxyartemisinin, *Tetrahedron Lett.*, 1989, 30, 5973–5976 and Jung, M.; Li, X.; Bustos, D. A.; ElSohly, H. N.; McChesney, J. D.; Milhous, W. K., Synthesis and Antimalarial Activity of (+)-Deoxoartemisinin, *J. Med. Chem.*, 1990, 33, 1516–1518).

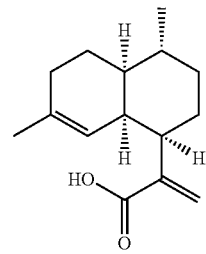
II

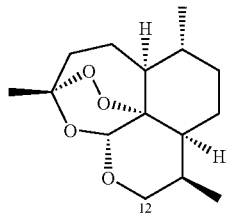
III

Non-acetal-type analogs of deoxoartemisinin recently received attention owing to their better bioavailability, such as acid stability, than acetal-type analogs. Furthermore, evidence that analogs not possessing exo-oxygen at C-12 are less neurotoxic in animal studies than acetal type artemisinin is also emerging and may thus lead to the future abandonment of the currently clinically used acetal-type analogs (e.g., arteether, artemether, artesunate and artelinic acid). After the preparation of 12-n-butyldeoxoartemisinin as the first hydrolytically stable non-acetal type analog containing a C—C bond at C-12 was reported, a series of non-acetal-type derivatives including a few of heteroaryl and unsaturated substituents a C-12 have been prepared (See Jung, M.; Bustos, D. A.; ElSohly, H. N.; McChesney, J. D., A Concise and Stereoselective Synthesis of (+)-12-n-Butyldeoxoartemisinin, *Synlett*, 1990, 743–744 and Chorki, F.; Crousse, B.; Bonnet-Delpon, D.; Begue, J. P.; Brigaud, T.; Portella, C., C-10 Fluorinated Derivatives of Dihydroartemisinin: Difluoromethylene Ketones, *Tetrahedron Lett.*, 2001, 42, 1487–1489).

Although most studies have focused on antimalarial activities, a few research groups have recently reported on cancer cell toxicity of artemisinin and it related derivatives. (see Woerdenbag, H. J.; Moskal, T. A.; Pras, N.; Maringle, T. M.; ElFeraly, F. S.; Kampinga, H. H.; Konings, A. W. T., Cytotoxicity of Artemisinin-related Endoperoxides to Ehrlich ascites Tumor cells, *J. Nat. Prod.*, 1993, 56, 849 and Wu, J-M.; Shan F.; Wu, G-S.; Li, Y.; Ding, J.; Xiao, D.; Han, J-X.; Atassi, G; Leonce, S.; Caignard, D-H.; Renard, P., Synthesis and Cytotoxicity of Artemisinin derivatives containing Cyanoarylmethyl group, *Eur. J. Med. Chem.*, 2001, 36(5), 469–479). Because of their higher rate of cell division, most cancer cells express a higher surface concentration of transferrin receptors than normal cells and have high rates of iron intake. A unique structure bearing endoperoxide could be a trigger for the generation of active oxygen radicals via hemolytic cleavage of the weak oxygen-peroxide bond accelerated by higher ferrous ion concentration of cancer cell, which may mediate for the selective and preferable damage to vital cellular structures of the relatively active cancer cells. Although some dimers of acetal type derivatives of artemisinin have been prepared and show anticancer activities, yields are low and most of them possess either aromatic linkers or still acetal types at the C-12 position, which are neurotoxic, acid unstable, and show low anticancer activities (see Galal, A. M.; Ahmad, M. S.; El-Feraly, F. S., Preparation and Characterization of a New Artemisinin-Derived Dimer, *J. Nat. Prod.*, 1996, 59, 917–920; Posner, G. H.; Ploypradith, P.; Parker, M. H.; O'Dowd, H.; Woo, S-H.; Northrop, J.; Krasavin, M.; Dolan, P.; Kensler, T. W.; Xie, S.; Shapiro, Antimalarial, Antiproliferative, and Antitumor Activities of Artemisinin-Derived, Chemically Robust, Trioxane Dimers., *J. Med. Chem.*, 1999, 42, 4275–4280; and Ekthawatchai, S.; Kamchonwongpaisan, S.; Kongsaeree, P.; Tarnchompoo, B.; Thebtaranonth, Y; Yuthavong, Y, C-16 Artemisinin Derivatives and Their Antimalarial and Cytotoxic Activities: Synthesis of Artemisinin Monomers, Dimers, Trimers, and Tetramers by Nucleophilic Additions to Artemisitene, *J. Med. Chem.*, 2001, 44, 4688–4695).

DISCLOSURE

Suprisingly, we found that deoxoartemisinin dimer and trimer had excellent anticancer activity, by preparing non-acetal-type deoxoartemisinin dimer and trimer having no linker containing C—O bonds, aromatic or unsaturated groups at C-12 position and then testing the anticancer activity thereof.

Accordingly, it is an object of the present invention to provide a deoxoartemisinin dimer and trimer having excellent anticancer activity.

It is another object of the present invention to easily prepare the deoxoartemisinin dimer and trimer in high yield.

It is another object of the present invention to provide anticancer agents comprising the deoxoartemisinin dimer and trimer.

It is another object of the present invention to provide a deoxoartemisinin monomer of intermediate for preparing the deoxoartemisinin dimer and trimer in high yield.

It is another object of the present invention to easily prepare the deoxoartemisinin monomer in high yield.

Deoxoartemisinin dimer and trimer of the present invention have the following formula (IV):

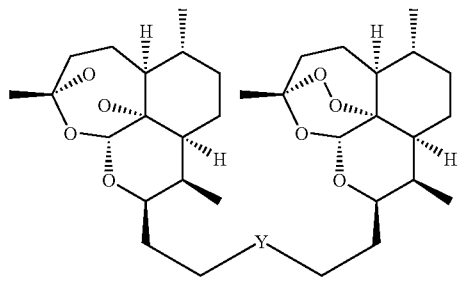

wherein Y is —S—, —SO$_2$—,

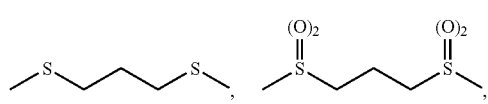

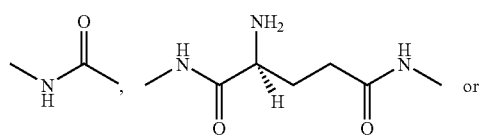

or

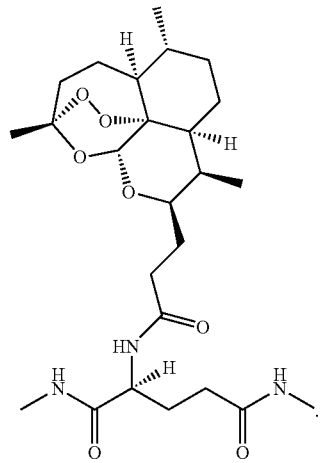

The deoxoartemisinin dimer and trimer of the present invention are prepared from the deoxoartemisinin monomers of formula (V) and (VI), respectively, as shown in Schemes 1, 2 and 3 below.

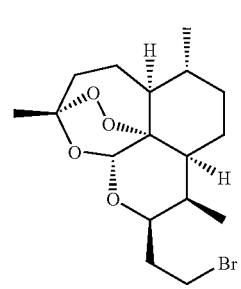

V

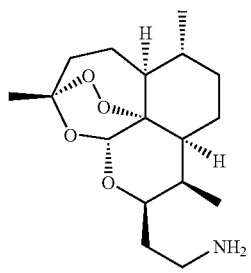

VI

The deoxoartemisinin dimer of the present invention having sulfide- or sulfonyl group-bearing linker is prepared by bis-nucleophilic coupling reaction of 12-bromoethyldeoxoartemisinin monomers (V), as shown in Scheme 1 below. Particularly, the deoxoartemisinin dimer (IVa$_1$) is prepared by reacting 1 mole of sodium sulfide with 2 moles of 12-bromoethyldeoxoartemisinin (V) and dimer (IVa$_2$) is prepared by oxidizing the dimer (IVa$_1$) with oxidizing agent such as meta-chloroperbenzoic acid (m-CPBA). In a similar fashion, the deoxoartemisinin dimer (IVb$_1$) is prepared by 1 mole of 1,3-propanedithiol with 2 moles of 12-bromoethyldeoxoartemisinin (V) and the dimer (IVb$_2$) is prepared by reacting the dimer (IVb$_1$) with an oxidizing agent such as m-CPBA.

Scheme 1

The deoxoartemisinin dimer of the present invention having amide groups-containing linker is prepared from 12-aminoethyldeoxoartemisinin (VI), as shown in Scheme 2 below. Particularly, the deoxoartemisinin dimer (IVc) is prepared by coupling 12-aminoethyldeoxoartemisinin (VI) with 12-carboxylethyldeoxoartemisinin (VII) in the presence of a catalyst such as 1-ethyl-3-(3-dimethylaminopropyl)carbodiimide(EDC)/10-hydroxybenzotriazole(HOBt).
On the other hand, the deoxoartemisinin dimer (IVd) is prepared by directly coupling 12-aminoethyldeoxoartemisinin (VI) with protected glutarate in the presence of a catalyst such as EDC/HOBt, removing the benzyl group of the ester, coupling the resultant product with 12-aminoethyldeoxoartemisinin (VI) in the presence of a catalyst such as EDC/HOBt and then deprotecting the t-BOC protected group of the amino group of the resultant product.

Scheme 2

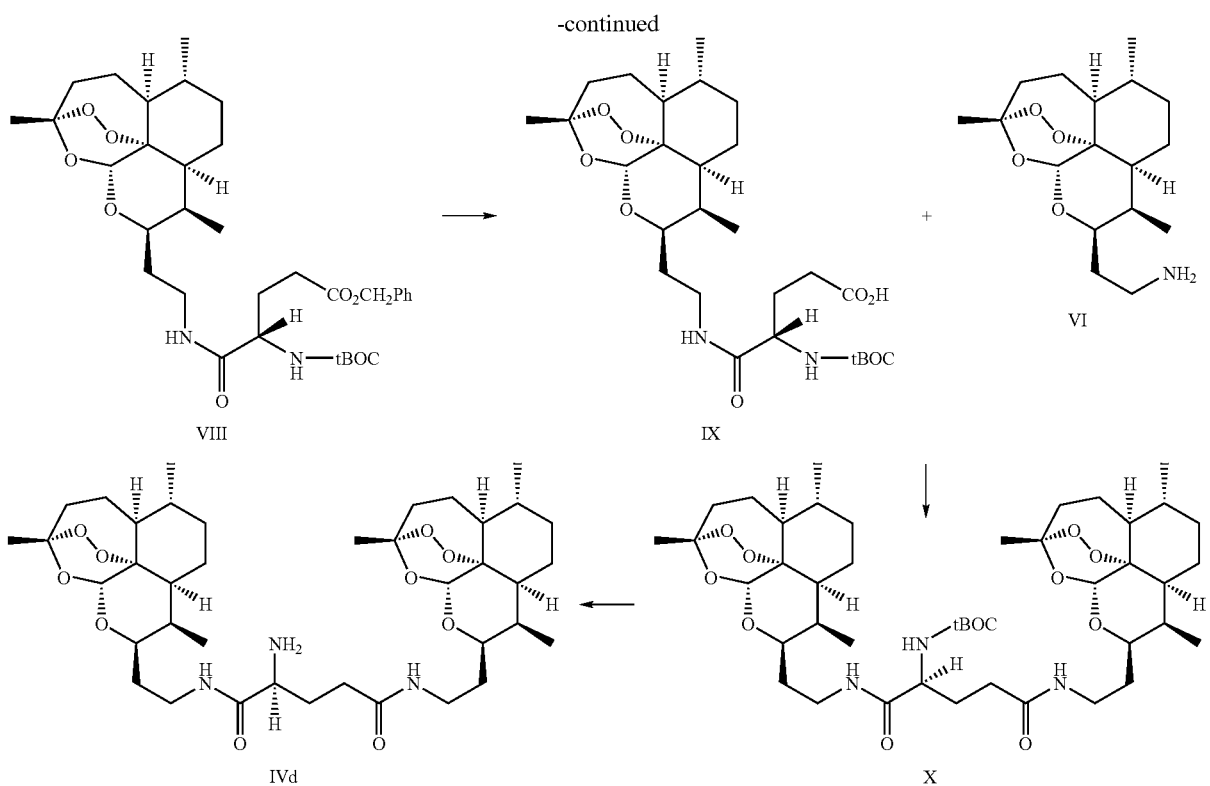

The deoxoartemisinin trimer (IVe) of the present invention is prepared by coupling 12-carboxylethyldeoxoartemisinin (VII) with L-glutamic diethylester in the presence of a catalyst such as EDC/HOBt, hydrolyzing the two ester groups of the product from the previous step and then doubly coupling the product from the previous step with 2 moles of 12-aminoethyldeoxoartemisinin (VI) in the presence of a catalyst such as EDC/HOBt, as shown in Scheme 3 below.

Scheme 3

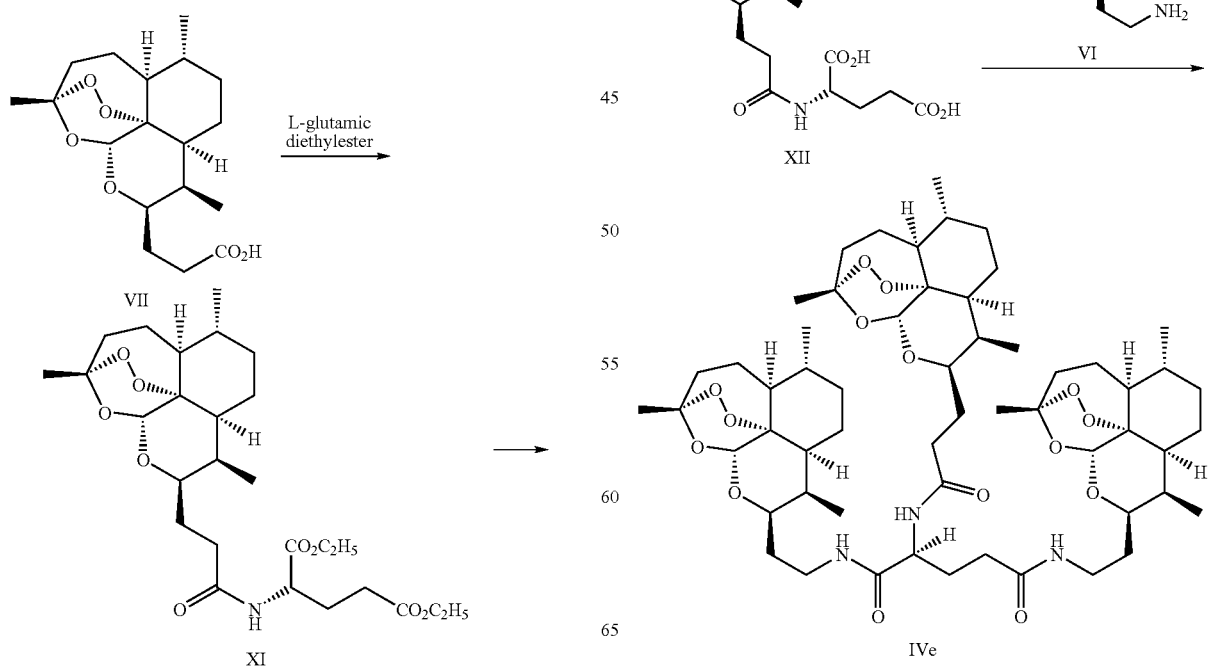

The novel deoxoartemisinin monomers (V and VI), which are intermediates for preparing the deoxoartemisinin dimer and trimer of the present invention, are prepared from 12-vinyldihydroartemisinyl alcohol (XIII), as shown in Scheme 4 below. A 12-vinyldihydroartemisinyl alcohol (XIII) can be synthesized from artemisinic acid (II) by a known synthetic route (see Jung et al., A Concise and Stereoselective Synthesis of (+)-12-n-Butyldeoxoartemisinin, *Synlett,* 1990, 743–744). Since artemisinin is much more expensive than artemisinic acid and a direct introduction of a C—C bond at C-12 of artemisinin may cause a destruction of the biologically essential endoperoxide, the artemisinic acid is used. Particularly, 12-bromoethyldeoxoartemisinin (V) is prepared by direct hydroborative oxidizing a terminal olefin of 12-vinyldihydroartemisinyl alcohol (XIII), brominating the resultant product with $CBr_4$/$PPh_3$, photooxygenative cyclizing the resultant product by a known procedure (see Jung, M et al., supra). On the other hand, 12-aminoethyldeoxoartemisinin (VI) is prepared by reacting 12-bromoethyldeoxoartemisinin (V) with sodium azide and then reducing the azide of the resultant product. In the preparation of 12-bromoethyldeoxoartemisinin (V) and 12-aminoethyldeoxoartemisinin (VI) according to the above-mentioned procedures, 12β-epimer is obtained exclusively.

The deoxoartemisinin dimer and trimer of the present invention is C-12 non-acetal-type and have no linker containing C—O bonds, aromatic or unsaturated groups at C-12 position, and thus is less neurotoxic, acid stable and have a higher anticancer activity. Therefore, the dimer and trimer of the present invention can be used as an effective anticancer agent for oral administration.

An anticancer agent containing the deoxoartemisinin dimer or trimer of the present invention as an effective constituent can be administered orally (e.g., ingestion or inhalation) or parenterally (e.g., intravenous injection, subcutaneous injection, percutaneous absorption, etc.) and can be prepared in the various form of tablets, capsules, granules, fine subtilae, powders, sublingual tablets, suppositories, ointments, injections, emulsions, suspensions, drug-treated syrups, etc., depending on its use. The above-mentioned various type of anticancer agents are prepared by a known technique using pharmaceutically acceptable conventional carrier such as excipient, binder, disintegrator, lubricant, antiseptic, antioxidant, isotonic agent, buffer, coating, sweeting, solubilizer, base, dispersion, stabilizer, colorant.

In the preparation of the agent, the content of the compounds of the present invention depends on the type of agents, but preferably ranges from 0.01 to 100% by weight.

The dosage of the anticancer agent of the present invention will vary depending on a variety of factors, such as, the Scheme 4 kind of mammalian including human to be treated, the severity of the disease and the physician's judgment. Typically, for oral administration, the anticancer agent of the present invention can be administered as an effective constituent in the amount of 0.01 to 50 mg per kg body weight per day and, for parenteral administration, in the amount of 0.01 to 10 mg per kg body weight per day.

The anticancer agent of the present invention can be administered at one time or at several times per day and its dosage can be varied depending on the severity of the disease and the physician's judgment.

The present invention is further described in the following examples. These examples illustrate the invention only and are not to be construed as limiting the scope of the present invention in any way.

EXAMPLES

Example 1

Synthesis of 12-(2'-bromoethyl)deoxoartemisinin (V)

(1) Synthesis of 12-(2'-hydroxyethyl)dihydroartemisinyl alcohol (XIV)

12-vinyldihydroartemisinyl alcohol (XII) (568 mg, 2.290 mmol), prepared by a known procedure (see Jung et al., A Concise and Stereoselective Synthesis of (+)-12-n-Butyldeoxoartemisinin, Synlett, 1990, 743–744), was slowly added to THF solution containing 0.5M of 9-borobicyclo[3.3.1]nonan (9BBN) (90.1 mL, 4.58 mmol) under nitrogen atmosphere and the resulting mixture was stirred at room temperature for 30 minutes. Then, to this solution was added 30%—$H_2O_2$/3N—NaOH (1/1, 2 mL) and the resulting solution was stirred at room temperature for 1 hour. The reaction mixture was extracted with ether (40 mL×2) and washed with saturated $NaHCO_3$ (20 mL) and brine (20 mL×2). The extract was dried over $MgSO_4$, concentrated in vacuo and purified by silica gel column (hexane/ethyl acetate=1/1 as eluent) to afford 12-(2'-hydroxyethyl)dihydroartemisinyl alcohol (XIV) as a colorless oil (97% yield).

$^1$H-NMR ($CDCl_3$, 250 MHz) δ5.15(s, 1H, H-5), 4.14(d, 1H, J=9.8 Hz, H-12), 3.89–3.80(m, 2H, H-2), 2.47(s, 1H), 1.94–1.72(m, 6H), 1.54(s, 3H, $CH_3$-15), 1.53–1.25(m, 9H), 0.84(d, 3H, J=7.3 Hz, $CH_3$-13), 0.87(d, 3H, J=6.6 Hz, $CH_3$-14).

$^{13}$C-NMR ($CDCl_3$, 63 MHz) δ135.5, 120.9, 72.0, 62.6, 42.6, 42.5, 39.7, 37.8, 37.6, 36.0, 28.1, 27.0, 26.4, 26.2, 24.1, 20.1, 10.4.

IR(neat) $u_{max}$ 3435(OH), 2921, 1647, 1622, 1386, 1124, 1088, 1016 cm$^{-1}$ MS(EI) m/z 266([M+]), 248([M+]—$H_2O$), 203([M+]—$C_2H_5O$).

(2) Synthesis of 12-(2'-bromoethyl)dihydroartemisinyl Alcohol (XV)

12-(2'-hydroxyethyl)dihydroartemisinyl alcohol (XIV) (399 mg, 1.503 mmol) was dissolved in dry $CH_2Cl_2$ (20 mL) and triphenylphosphine (TPP) (393 mg, 1.503 mmol) was added. The solution was allowed to stir at 0° C. for 30 minutes. The reaction mixture was warmed to room temperature. To this reaction mixture was slowly added $CBr_4$ (498 mg, 1.503 mmol). The reaction was allowed to stir at room temperature for 30 minutes and was quenched with methanol (10 mL). The reaction mixture was extracted with ethyl acetate (20 mL×3) and was washed with brine (20 mL×2). The extract was dried over $MgSO_4$, concentrated in vacuo and purified by silica gel column (hexane/ethyl acetate=5/2 as eluent) to afford 12-(2'-bromoethyl)dihydroartemisinyl alcohol (XV) (470 mg, 95%) as a colorless oil.

$^1$H-NMR($CDCl_3$, 250 MHz) δ5.14(s, 1H, H-5), 4.1(d, 1H, J=7.5 Hz, H-12), 3.57–3.52(t, 2H, J=7.5 Hz), 2.31(s, 1H), 1.94–1.71(m, 6H), 1.54(s, 3H, $CH_3$-15), 1.53–1.25(m, 9H), 0.84(d, 6H, J=5.0 Hz, $CH_3$-13,14).

$^{13}$C-NMR($CDCl_3$, 63 MHz) δ135.5, 120.7, 69.8, 42.8, 42.4, 39.1, 38.9, 37.8, 36.0, 31.9, 28.0, 27.0, 26.4, 26.1, 24.1, 20.1, 10.2.

IR(neat) $u_{max}$ 3427(OH), 2910, 1726, 1447, 1378, 1259, 992, 908, 734 cm$^{-1}$ MS(EI) m/z 328([M+]), 310([M+]—$H_2O$), 249([M+]—Br).

(3) Synthesis of the Title Compound 12-(2'-bromoethyl)dihydroartemisinyl alcohol (XV)(250 mg, 0.665 mmol) was added to $CH_3CN/CH_2Cl_2$ (1/1, 60 mL) containing catalytic Rose Bengal and then was irradiated with white light (500 W tungsten lamp) at −23° C. for 4 hours under oxygen. After completion of the reaction, to the reaction mixture was added saturated $NaHCO_3$ solution (50 mL). This mixture was extracted with diethyl ether (20 mL×3) and then washed with brine (20 mL×2). The extract was dried over $MgSO_4$. Solvent was evaporated under reduced pressure and the residue was dissolved in $CH_3CN/CH_2Cl_2$ (9/1, 10 mL). This solution was cooled to −40° C. Acidic catalyst trifluoroacetic acid (TFA) was added to this solution and then was allowed to stir at −40° C. for 12 hours under oxygen. The reaction mixture was quenched with saturated $NH_4Cl$ solution (10 mL) and extracted with diethyl ether (20 mL×3). The extract was washed with water (30 mL×2) and brine (30 mL×2), dried over $MgSO_4$, concentrated in vacuo and purified by silica gel column (hexane/ethyl acetate=5/1 as eluent) to afford 12-(2'-bromoethyl)deoxoartemisinin (V)(99 mg, 40%) as a white solid.

$[α]^{18}{}_D$=+96.3(c 0.1, $CHCl_3$).

m.p. 94° C.

$^1$H-NMR($CDCl_3$, 500 MHz) δ5.26(s, 1H, H-5), 4.33–4.27 (m, 1H, H-12), 3.56–3.51(m, 2H, H-2'), 2.60–2.45(m, 2H), 2.30(ddd, 1H, J=4.1, 3.8, 4.1 Hz), 2.05–1.89(m, 4H), 1.83–1.48(m, 4H), 1.39(s, 3H, $CH_3$-15), 1.28–1.22(m, 2H), 0.94(d, 3H, J=4.8 Hz, $CH_3$-13), 0.87(d, 3H, J=7.4 Hz, $CH_3$-14), 0.78(m, 1H).

$^{13}$C-NMR($CDCl_3$, 125 MHz) δ103.4, 89.5, 81.2, 73.2, 52.4, 44.4, 37.7, 37.3, 35.8, 34.8, 33.7, 31.6, 30.3, 26.3, 25.0, 20.4, 13.1.

IR(KBr) $u_{max}$ 2950, 1451, 1377, 1272, 1117, 1042, 1010, 880(O—O), 756 cm$^{-1}$ MS(EI) m/z 376(M+2), 342([M+]-$O_2$).

Example 2

Synthesis of 12-(2'-aminoethyl)deoxoartemisinin (VI)

(1) Synthesis of 12-(2'-ethyl azide)deoxoartemisinin (XVI)

12-(2'-bromoethyl)deoxoartemisinin (V) (128 mg, 0.352 mmol) was dissolved in DMF (5 mL) and sodium azide (45.7 mg, 0.704 mmol) was added. This mixture was allowed to stir at room temperature for 5 hours. To the reaction mixture was added water (30 mL). The resulting mixture was extracted with ethyl acetate (50 mL×2) and then washed with brine (40 mL×2). The extract was dried over $MgSO_4$, concentrated in vacuo, then purified by silica gel column (hexane/ethyl acetate=5/2 as eluent) to afford 12-(2'-ethyl azide)deoxoartemisinin (XVI) (109 mg, 92%) as a colorless oil.

$[\alpha]^{23}_D$=+64.2(c 0.47, CHCl$_3$).

$^1$H-NMR (CDCl$_3$, 250 MHz) δ5.28(s, 1H, H-5), 4.31–4.27(m, 1H, H-12), 3.56–3.53(m, 1H), 3.44–3.38(m, 1H), 2.69–2.64(m, 1H), 2.31(ddd, 1H, J=4.1, 3.8, 4.1 Hz), 2.03–1.75(m, 5H), 1.67–1.60(m, 3H), 1.40(s, 3H, CH$_3$-15), 1.33–1.27(m, 3H), 0.96(d, 3H, J=5.6 Hz, CH$_3$-13), 0.87(d, 3H, J=7.5 Hz, CH$_3$-14), 0.82(m, 1H).

$^{13}$C-NMR (CDCl$_3$, 63 MHz) δ103.5, 89.5, 81.3, 72.3, 52.5, 49.8, 44.5, 37.8, 36.9, 34.7, 30.4, 29.5, 26.3, 25.1, 25.1, 20.4, 13.1.

IR(neat) u$_{max}$ 2927, 2875, 2095(N$_3$), 1733, 1454, 1377, 1277, 1098, 1011, 880(O—O), 756 cm$^{-1}$ MS(EI) m/z 337[M+], 305([M+]-O$_2$).

(2) Synthesis of the Title Compound 12-(2'-ethylazide)deoxoartemisinin (XVI) (137.9 mg, 0.352 mmol) was dissolved in dry THF (10 mL), cooled to −78° C. and LAH (35.1 mg, 0.925 mmol) was added. The solution was allowed to stir at −78° C. for 1 hour, warmed to −10° C. slowly and allowed to stir at that temperature for 1 hour. The reaction mixture was extracted with ethyl acetate (50 mL×2) and washed with brine (40 mL×2). The extract was dried over MgSO$_4$, concentrated in vacuo, then purified by silica gel column (100% methanol as eluent) to afford 12-(2'-aminoethyl)deoxoartemisinin (VI) (85.4 mg, 78%) as a white solid.

$[\alpha]^{23}_D$=+38.7 (c 0.1, CHCl$_3$).

m.p. 103° C.

$^1$H-NMR (CDCl$_3$, 250 MHz) δ5.32(s, 1H, H-5), 4.29–4.21(m, 1H, H-12), 2.93–2.84(m, 3H), 2.69–2.64(m, 1H), 2.32(ddd, 1H, J=4.0, 3.7, 4.0 Hz), 2.05–1.82(m, 3H), 1.80–1.74(m, 2H), 1.62–1.50(m, 2H), 1.40(s, 3H, CH$_3$-15), 1.32–1.26(m, 4H), 0.96(d, 3H, J=5.7 Hz, CH$_3$-13), 0.87(d, 3H, J=7.5 Hz, CH$_3$-14), 0.83(m, 1H).

$^{13}$C-NMR (CDCl$_3$, 63 MHz) δ103.5, 89.4, 81.5, 74.2, 52.7, 44.7, 41.0, 37.8, 36.9, 34.8, 33.2, 30.6, 26.5, 25.1, 25.0, 20.5, 13.4.

IR(KBr) u$_{max}$ 3365(NH), 2924, 2874, 1663, 1570, 1455, 1377, 1114, 1054, 1011, 944, 877(O—O), 753 cm$^{-1}$ HRMS(FAB) m/z 312.2175([M+H]$^+$, obsd), 311.2097 (calcd for C$_{17}$H$_{29}$NO$_4$).

Elemental analysis (C$_{17}$H$_{29}$NO$_4$) C, H, N.

Example 3

Synthesis of 12-(2'-ethylsulfide)deoxoartemisinin Dimer (IVa$_1$)

12-(2'-bromoethyl)deoxoartemisinin (V) (45 mg, 0.124 mmol) was dissolved in pure ethanol (4 mL), allowed to stir at room temperature for 10 minutes and Na$_2$S (4.8 mg, 0.5 eq) was added. The reaction mixture was allowed to stir at room temperature for 7 hours. This reaction mixture was extracted with ethyl acetate (10 mL×3) and washed with brine (10 mL×2). The extract was dried over MgSO$_4$, concentrated in vacuo, then purified by silica gel column (hexane/ethyl acetate=5/1 as eluent) to afford 12-(2'-ethylsulfide)deoxoartemisinin dimer (IVa$_1$) (58.7 mg, 76%) as a colorless oil.

$[\alpha]^{25}_D$=+58.7 (c 0.23, CHCl$_3$).

$^1$H-NMR (CDCl$_3$, 250 MHz) δ5.29(s, 2H, H-5), 4.24–4.19(m, 2H, H-12), 2.91–2.84(m, 2H), 2.71–2.70(m, 2H), 2.55–2.49(m, 2H), 2.33(ddd, 2H, J=3.1, 3.5, 4.0 Hz), 2.03–1.78(m, 8H), 1.67–1.55(m, 10H), 1.41(s, 6H, CH$_3$-15), 1.36–1.26(m, 4H), 0.96(d, 6H, J=5.8 Hz, CH$_3$-13), 0.88(d, 6H, J=7.4 Hz, CH$_3$-14), 0.83(m, 2H).

$^{13}$C-NMR (63 MHz, CDCl$_3$) δ103.6, 89.2, 81.4, 76.8, 75.5, 52.7, 44.8, 37.7, 36.9, 34.8, 30.5, 30.1, 26.5, 25.2, 25.0, 20.6, 13.5.

IR(neat) u$_{max}$ 2925, 2876, 1617, 1459, 1379, 1119, 1054, 1011, 887(O—O), 735 cm$^{-1}$ HRMS(FAB) m/z 645.3541([M+Na]$^+$, obsd), 622.3539 (calcd for C$_{34}$H$_{54}$O$_8$S).

Elemental analysis (C$_{34}$H$_{54}$O$_8$S) C, H, S.

Example 4

Synthesis of 12-(2'-sulfonylethyl)deoxoartemisinin dimer (IVa$_2$)

12-(2'-ethylsulfide)deoxoartemisinin dimer (IVa$_1$) (28 mg, 0.041 mmol) was dissolved in dry CH$_2$Cl$_2$ (2 mL), allowed to stir at room temperature for 10 minutes and m-CPBA (15.7 mg, 0.091 mmol) was added slowly. The reaction mixture was allowed to stir at room temperature for 3 h and saturated NaHCO$_3$ solution (3 mL) was added. The reaction mixture was extracted with ethyl acetate (10 mL×3) and washed with brine (10 mL×2). The extract was dried over MgSO$_4$, concentrated in vacuo, then purified by silica gel column (hexane/ethyl acetate=2/1 as eluent) to afford 12-(2'-sulfonylethyl)deoxoartemisinin dimer (IVa$_2$) (24.6 mg, 91%) as a white solid.

$[\alpha]^{20}_D$=+84.2 (c 0.44, CHCl$_3$).

m.p. 98° C.

$^1$H-NMR (CDCl$_3$, 250 MHz) δ5.30(s, 2H, H-5), 4.25–4.18(m, 2H, H-12), 3.53–3.41(m, 2H, H-2), 3.05–2.935(m, 2H, H-2), 2.79–2.71(m, 2H), 2.36(ddd, 2H, J=3.2, 3.5, 4.1 Hz), 2.17–1.92(m, 6H), 1.88–1.78(m, 4H), 1.69–1.49(m, 8H), 1.39(s, 6H, CH$_3$-15), 0.97(d, 6H, J=5.7 Hz, CH$_3$-13), 0.92(d, 6H, J=7.6 Hz, CH$_3$-14), 0.89(m, 2H).

$^{13}$C NMR (CDCl$_3$, 63 MHz) δ134.1, 130.6, 130.1, 128.6, 103.6, 89.4, 81.4, 74.1, 52.5, 44.4, 36.8, 30.5, 26.4, 25.2, 22.4, 20.4, 13.2.

IR(KBr) u$_{max}$ 2928, 2876, 1723, 1575, 1449, 1380, 1280, 1123, 1052, 880(O—O), 734 cm$^{-1}$ HRMS(FAB) m/z 677.3335([M+Na]$^+$, obsd), 654.3438 (calcd for C$_{34}$H$_{64}$O$_{10}$S).

Elemental analysis (C$_{34}$H$_{64}$O$_{10}$S) C, H, S.

Example 5

Synthesis of S,S'-[12-(2'-ethyl)deoxoartemisinin] dithiopropane dimer (IVb$_1$)

Powdered KOH (12.36 mg, 0.22 mmol) was added to DMSO (2 mL), allowed to stir at room temperature for 1 hour and then 1,3-propanedithiol (6.64 µl, 0.054 mmol) and 12-(2'-bromoethyl)deoxoartemisinin (V) (41 mg, 0.112 mmol) was added together. The reaction mixture was allowed to stir at room temperature for 1 hour. The reaction mixture was extracted with ethyl acetate (30 mL×3) and washed with brine (20 mL×2). The extract was dried over MgSO$_4$, concentrated in vacuo, then purified by silica gel column (hexane/ethyl acetate=5/2 as eluent) to afford S,S'-[12-(2'-ethyl)deoxoartemisinin]dithiopropane dimer (IVb$_1$) (50.7 mg, 65%) as a colorless oil.

$[\alpha]^{24}_D$=+112.3(c 0.4, CHCl$_3$).

$^1$H-NMR (CDCl$_3$, 250 MHz) δ5.29(s, 2H, H-5), 4.22–4.17(m, 2H, H-12), 2.83–2.66(m, 10H), 2.41–2.29(m, 2H), 2.05–1.76(m, 10H), 1.66–1.53(m, 10H), 1.41(s, 6H,

CH3-15), 1.33–1.26(m, 4H), 0.96(d, 6H, J=5.7 Hz, CH$_3$-13) 0.88(d, 3H, J=7.5 Hz, CH$_3$-14), 0.83(m, 2H).

$^{13}$C-NMR(CDCl$_3$, 63 MHz) δ103.6, 89.3, 81.4, 75.3, 52.7, 44.7, 38.8, 37.8, 36.9, 34.8, 32.2, 30.5, 30.2, 29.1, 26.5, 25.2, 25.0, 20.5, 13.4.

IR(neat) u$_{max}$ 2928, 2873, 1655, 1719, 1452, 1378, 1215, 1120, 1036, 877(O—O), 755 cm$^{-1}$ HRMS(FAB) m/z 719.3701([M+Na]$^+$, obsd) 696.3730 (calcd for C$_{37}$H$_{60}$O$_8$S$_2$).

Elemental analysis (C$_{37}$H$_{60}$O$_8$S$_2$) C, H, S.

Example 6

Synthesis of S,S'-[12-(2'-ethyl)deoxoartemisinin] disulfonylpropane Dimer (IVb$_2$)

S,S'-[12-(2'-ethyl)deoxoartemisinin]disulfonylpropane dimer (IVb$_2$) (22.6 mg, 72%) as a white solid was prepared by following the procedure of Example 4, but replacing 12-(2'-ethylsulfide)deoxoartemisinin dimer (IVa$_1$) with S,S'-[12-(2'-ethyl)deoxoartemisinin]dithiopropane dimer (IVb$_1$) (29 mg, 0.041 mmol) and using 31.1 mg of m-CPBA (0.18 mmol).

[α]$^{25}_D$=+110.4(c 0.47, CHCl$_3$).

m.p. 138° C.

$^1$H-NMR (CDCl$_3$, 250 MHz) δ5.30(s, 2H, H-5), 4.25–4.21(m, 2H, H-12), 3.49–3.43(m, 2H), 3.26(t, 2H, J=7.1 Hz), 3.04–2.92(m, 2H), 2.74–2.62(m, 2H), 2.49–2.43 (m, 2H), 2.08–1.94(m, 8H), 1.89–1.75(m, 4H), 1.69–1.59 (m, 8H), 1.39(s, 6H, CH$_3$-15), 1.34–1.27(m, 4H), 0.97(d, 6H, J=5.7 Hz, CH$_3$-13), 0.91(d, 6H, J=7.6 Hz, CH$_3$-14), 0.88(m, 2H).

$^{13}$C-NMR(CDCl$_3$, 63 MHz) δ134.2, 130.6, 130.1, 128.4, 103.6, 89.5, 81.4, 74.1, 52.5, 44.3, 37.7, 36.8, 34.7, 31.3, 30.5, 26.4, 25.2, 20.4, 13.5.

IR(KBr) u$_{max}$ 2926, 2875, 1720, 1584, 1495, 1387, 1310, 1130, 1052, 877(O—O), 756, 465 cm$^{-1}$ HRMS(FAB) m/z 783.3538([M+Na]$^+$, obsd), 760.3526 (calcd for C$_{37}$H$_{60}$O$_{12}$S$_2$).

Elemental analysis (C$_{37}$H$_{60}$O$_{12}$S$_2$) C, H, S.

Example 7

Synthesis of 12-(2'-amidethyl)deoxoartemisinin Dimer (IVc)

12-carboxylethyldeoxoartemisinin (VII) (32 mg, 0.086 mmol), prepared by a known procedure (see Jung, M.; Freitas, A. C. C.; McChesney, J. D.; ElSohly, H. N., A Practical and General Synthesis of (+)-Carboxyalkyldeoxoartemisinins, *Heterocycles*. 1994, 39, 23–29), was dissolved in dry CH$_2$Cl$_2$ (3 mL) and HOBt (38 mg, 0.256 mmol) and EDC (47 mg, 0.256 mmol) was added together. The reaction mixture was allowed to stir at room temperature for 30 minutes and 12-(2'-aminoethyl)deoxoartemisinin (VI) (30 mg, 0.096 mmol) was added. The resulting reaction mixture was allowed to stir at room temperature for 4 hours. The reaction mixture was extracted with ethyl acetate (20 mL×3) and washed with brine (10 mL×2). The extract was dried over MgSO$_4$, concentrated in vacuo, then purified by silica gel column (hexane/ethyl acetate=1/2 as eluent) to afford 12-(2'-aminoethyl)deoxoartemisinin dimer (IVc) in 81% yield as a colorless oil.

[α]$^{23}_D$=+111.3 (c 0.38, CHCl$_3$).

$^1$H-NMR (CDCl$_3$, 500 MHz) δ6.28(s, 1H, NH), 5.30(s, 1H, H-5), 5.29(s, 1H, H-5), 4.33–4.31(m, 1H, H-12), 4.06–4.04(m, 1H, H-12), 3.58–3.56(m, 1H, H-2), 3.28–3.26 (m, 1H, H-2), 2.73–2.69(m, 1H), 2.65–2.62(m, 1H), 2.51–2.44(m, 1H), 2.35–2.32(t, 2H, J=13.5 Hz), 2.24–2.15 (m, 1H), 2.04–1.98(m, 2H), 1.95–1.89(m, 3H), 1.78–1.71 (m, 4H), 1.66–1.64(M, 4H), 1.40(s, 6H, CH$_3$-15), 1.37–1.24 (m, 9H), 0.96(d, 3H, J=5.3 Hz, CH$_3$-13), 0.95(d, 3H, J=5.7 Hz, CH$_3$-13), 0.88(d, 3H, J=7.5 Hz, CH$_3$-14), 0.86(d, 3H, J=7.5 Hz, CH$_3$-14), 0.84(m, 2H).

$^{13}$C-NMR (CDCl$_3$, 63 MHz,) δ173.8, 126.8, 126.1, 118.0, 111.2, 103.7, 103.5, 89.6, 89.0, 81.5, 81.4, 76.4, 74.7, 52.8, 52.5, 44.8, 44.3, 37.8, 37.6, 36.8, 35.1, 34.8, 34.7, 30.7, 30.5, 26.5, 26.4, 25.4, 25.1, 25.0, 20.5, 20.4, 13.7, 13.6.

IR(neat) u$_{max}$ 3380(NH), 2941, 2877, 1653(C=O), 1545, 1446(C—N), 1379, 1097, 1051, 1013, 915, 878(O—O), 733 cm$^{-1}$ HRMS(FAB) m/z 634.3995([M+H]$^+$, obsd), 633.3877 (calcd for C$_{35}$H$_{55}$NO$_9$).

Elemental analysis (C$_{35}$H$_{55}$NO$_9$) C, H, N.

Example 8

Synthesis of 12-[2'-(N-glutamic)-α,β-amide] deoxoartemisinin Dimer (IVd)

(1) Synthesis of 12-[2'-(N-tBOC-glutamic-γ-benzylester)-α-amide]deoxoartemisinin (VIII)

N-tBOC-L-glutamic acid-γ-benzylester (35 mg, 0.11 mmol) was dissolved in dry CH$_2$Cl$_2$ (5 mL) and HOBt (52 mg, 0.342 mmol) and EDC (63 mg, 0.342 mmol) was added. The reaction mixture was allowed to stir at room temperature for 30 minutes and 12-(2'-aminoethyl)deoxoartemisinin (VI) (42 mg, 0.135 mmol) was added. The resulting reaction mixture was allowed to stir at room temperature for 3 hours. The reaction mixture was extracted with ethyl acetate (20 mL×3) and washed with brine (10 mL×2). The extract was dried over MgSO$_4$, concentrated in vacuo, then purified by silica gel column (hexane/ethyl acetate=1/2 as eluent) to afford 12-[N-tBOC-glutamic-γ-benzylester)-α-amide] deoxoartemisinin (VIII) (71.5 mg, 84%) as a colorless oil.

[α]$^{25}_D$=+73.6 (c 0.47, CHCl$_3$).

$^1$H-NMR (CDCl$_3$, 250 MHz) δ7.36(s, 5H, aromatic H), 7.02(br, 1H, NH), 5.33(s, 1H, H-5), 5.11(s, 2H, benzyl), 4.40–4.39(m, 1H, H-12), 4.29–4.27(m, 1H), 4.15–4.13(m, 1H), 3.58–3.56(m, 1H, H-2), 3.28–3.24(m, 1H, H-2), 2.61–2.43(m, 3H), 2.36–2.14(m, 3H), 2.12–1.98(m, 4H), 1.91–1.65(m, 4H), 1.44(s, 9H, t-BOC), 1.42(s, 3H, CH$_3$-15), 1.35–1.26(m, 3H), 0.96(d, 3H, J=5.6 Hz, CH$_3$-13), 0.85(d, 3H, J=7.6 Hz, CH$_3$-14), 0.82(m, 1H).

$^{13}$C-NMR (CDCl$_3$, 63 MHz) δ173.2, 171.5, 155.2, 136.1, 128.8, 128.8, 128.5, 128.5, 128.4, 128.4, 103.8, 89.9, 81.3, 74.4, 66.6, 61.2, 53.1, 52.3, 44.0, 39.4, 37.7, 36.7, 34.6, 30.8, 28.6, 28.5, 28.5, 26.2, 25.1, 25.0, 20.4, 12.6.

IR(neat) u$_{max}$ 3364(NH), 2932, 2876, 1736(C=O), 1663 (C=O), 1538, 1453, 1393, 1249, 1163, 1051, 880(O—O), 702, 610 cm$^{-1}$ HRMS(FAB) m/z 631.3507([M+H]$^+$, obsd), 630.3516 (calcd for C$_{34}$H$_{50}$N$_2$O$_9$).

(2) Synthesis of 12-[2'-(N-tBOC-glutamic acid)-α-amide]deoxoartemisinin (IX)

12-[2'-(N-tBOC-glutamic-γ-benzylester)-α-amide] deoxoartemisinin (VIII) (36 mg, 0.057 mmol) was dissolved in dry THF/H$_2$O (1/1, 5 mL) and 1N LiOH (1 mL) was added. The solution was allowed to stir at room temperature for 2 hours. The reaction solution was acidified with 1N HCl, extracted with ethyl acetate (20 mL×3), and then washed with brine (10 mL×2). The extract was dried over MgSO$_4$, concentrated in vacuo, then purified by silica gel column (hexane/ethyl acetate=1/2 as eluent) to afford 12-[2'-(N-tBOC-glutamic acid)-α-amide]deoxoartemisinin (IX) (26.8 mg, 87%) as a colorless oil.

[α]$^{25}_D$=+66.4 (c 0.34, CHCl$_3$).

$^1$H—NMR(CDCl$_3$, 250 MHz) δ5.60(d, 1H, J=7.9 Hz, NH), 5.33(s, 1H, H-5), 4.34–4.32(m, 1H, H-12), 4.20–4.15(m, 1H), 3.49–3.47(m, 1H, H-2), 3.33–3.31(m, 1H, H-2), 2.66–2.58(m, 1H), 2.48–2.40(m, 2H), 2.30(ddd, 1H, J=2.2, 1.9, 3.7 Hz), 2.03–1.73(m, 5H), 1.67–1.61(m, 6H), 1.41(s, 9H, t-BOC), 1.38(s, 3H, CH$_3$-15), 1.33–1.21(m, 3H), 0.95(d, 3H, J=5.1 Hz, CH$_3$-13), 0.84(d, 3H, J=7.4 Hz, CH$_3$-14), 0.81(m, 1H).

$^{13}$C-NMR ((CDCl$_3$, 63 MHz,) δ176.6, 172.2, 103.7, 89.7, 81.4, 76.9, 74.7, 53.4, 52.5, 44.3, 39.1, 37.8, 36.8, 34.7, 30.7, 30.6, 29.8, 28.7, 28.7, 28.7, 28.7, 26.2, 25.2, 25.0, 20.5, 13.0.

IR(neat) u$_{max}$ 3352(CO$_2$H and NH), 2933, 2879, 1714 (C=O), 1657(C=O), 1533, 1459, 1379, 1275, 1170, 1053, 914, 882(O—O), 733 cm$^{-1}$ LCMS(ESI) m/z 540([M+]).

(3) Synthesis of 12-[2'-(N-tBOC-glutamic)-α,β-amide]deoxoartemisinin Dimer (X)

12-[2'-(N-tBOC-glutamic acid)-α-amide]deoxoartemisinin (IX) (21 mg, 0.039 mmol) was dissolved in dry CH$_2$Cl$_2$ (2 mL) and HOBt (22 mg, 0.119 mmol) and EDC (29 mg, 0.119 mmol) were added together. The reaction mixture was allowed to stir at room temperature for 30 minutes and 12-(2'-aminoethyl)deoxoartemisinin (VI) (18 mg, 0.058 mmol) was added. The resulting reaction mixture was allowed to stir at room temperature for 3 hours. The reaction mixture was extracted with ethyl acetate (20 mL×3) and washed with brine (10 mL×2). The extract was dried over MgSO$_4$, concentrated in vacuo, then purified by silica gel column (hexane/ethyl acetate=1/2 as eluent) to afford 12-[2'-(N-tBOC-glutamic)-α,β-amide]deoxoartemisinin dimer (X)(16.6 mg, 51%) as a colorless oil.

[α]$^{25}_D$=+114.6(c 0.46, CHCl$_3$).

$^1$H-NMR (CDCl$_3$, 250 MHz) δ6.71(s, 1H, NH), 5.87(s, 1H, NH), 5.34(s, 1H, H-5) 1H, H-5), 4.34–4.31(m, H-12), 4.13–4.10(m, 1H), 3.53–3.48(m, 2H), 3.25–3.23(m, 2H), 2.62–2.60(m, 2H), 2.39–2.29(m, 6H), 2.05–1.88(m, 8H), 1.86–1.62(m, 12H), 1.43(s, 9H, t-BOC), 1.39(s, 6H, CH$_3$-15), 1.28–1.25(m, 5H), 0.96(d, 6H, J=5.3 Hz, CH$_3$-13), 0.86(d, 6H, J=7.5 Hz, CH$_3$-14), 0.83(m, 2H).

$^{13}$C-NMR (CDCl$_3$, 63 MHz,) δ173.3, 173.2, 171.5, 171.4, 103.5, 103.4, 89.8, 89.6, 81.4, 81.4, 76.9, 74.3, 52.5, 52.5, 44.4, 44.3, 39.3, 37.8, 36.8, 34.7, 30.8, 28.9, 28.7, 26.4, 25.2, 25.1, 20.5, 14.5, 13.0, 12.8.

IR(neat) u$_{max}$ 3379(NH), 2877, 1713(C=O), 1656 (C=O), 1545, 1451, 1379, 1268, 1030, 917, 880(O—O), 732 cm$^{-1}$ LCMS(ESI) m/z 834([M+H]).

(4) Synthesis of the Title Compound

12-[2'-(N-tBOC-glutamic)-α,β-amide]deoxoartemisinin dimer (X) (28 mg, 0.036 mmol) was dissolved in dry CH$_2$Cl$_2$ (2 mL). To this solution was slowly added TFA (4.92 mg, 1.2 eq) at 0° C. for 30 minutes. The resulting reaction mixture was allowed to stir at 0° C. for 4 hours, extracted with ethyl acetate (20 mL×3) and washed with brine (10 mL×2). The extract was dried over MgSO$_4$, concentrated in vacuo, then purified by silica gel column (hexane/ethyl acetate=1/2 as eluent) to afford 12-[2'-(N-glutamic)-α,β-amide]deoxoartemisinin dimer (IVd) (19 mg, 72%) as a colorless oil. The dimer (IVd) is five times more water soluble (5.21 mg/ml) than artemisinin.

[α]$^{25}_D$=+120.8 (c 0.48, CHCl$_3$).

$^1$H-NMR (CDCl$_3$, 250 MHz) δ6.83(s, 1H, NH), 5.74(s, 1H, NH), 5.34(s, 1H, h-5), 5.31(s, 1H, H-5), 4.35–4.33(m, 2H, H-12), 4.15–4.12(m, 1H), 3.53–3.49(m, 2H), 3.27–3.24 (m, 2H), 2.64–2.62(m, 2H), 2.32–2.30(m, 2H), 2.15–1.58 (m, 12H), 1.53–1.41(m, 10H), 1.39(s, 6H, CH$_3$-15), 1.34–1.28(m, 6H), 0.97(d, 6H, J=5.3 Hz, CH$_3$-14), 0.86(d, 6H, J=7.5 Hz, CH$_3$-14), 0.82(m, 2H).

$^{13}$C-NMR (63 MHz, CDCl$_3$) δ173.4, 173.3, 171.5, 171.3, 103.6, 103.4, 89.8, 89.7, 84.4, 84.3, 76.9, 74.3, 52.6, 52.4, 44.5, 44.3, 39.3, 37.9, 36.7, 34.6, 30.9, 30.8, 28.7, 26.4, 25.2, 25.1, 20.5, 20.4, 14.5, 13.3, 12.7.

IR(neat) u$_{max}$ 3367(NH), 3098(NH), 2956, 2868, 1689 (C=O), 1558, 1446, 1380, 1209, 1137, 998, 887(O—O), 847, 757, 729 cm$^{-1}$ HRMS(FAB) m/z 734.4592([M+H]$^+$, obsd), 733.4513 (calc for C$_{39}$H$_{63}$N$_3$O$_{10}$).

Elemental analysis (C$_{39}$H$_{63}$N$_3$O$_{10}$) C, H, N.

Example 9

Synthesis of Deoxoartemisinin Trimer (IVe)

(1) Synthesis of N-[12-(β-deoxoartemisinin)propionyl]-L-glutamic diethyl ester (XI)

12-carboxylethyldeoxoartemisinin (VII)(32 mg, 0.256 mmol) was dissolved in dry CH$_2$Cl$_2$ (3 mL) and HOBt (38 mg, 0.256 mmol) and EDC (47 mg, 0.256 mmol) were added together. The reaction mixture was allowed to stir at room temperature for 30 minutes and L-glutamic diethylester (36 mg, 0.171 mmol) was added. The resulting reaction mixture was allowed to stir at room temperature for 3 hours. The reaction mixture was extracted with ethyl acetate (20 mL×3) and washed with brine (10 mL×2). The extract was dried over MgSO$_4$, concentrated in vacuo, then purified by silica gel column (hexane/ethyl acetate=1/2 as eluent) to afford N-[12-(β-deoxoartemisinin)propionyl]-L-glutamic diethylester (XI) (37.9 mg, 84%) as a colorless oil.

[α]$^{25}_D$=+44.5 (c 0.47, CHCl$_3$).

$^1$H-NMR (CDCl$_3$, 250 MHz,) δ6.31(d, 1H, J=7.5 Hz, NH), 5.29(s, 1H, H-5), 4.63–4.56(m, 1H), 4.23–4.08(m, 5H), 2.75–2.71(m, 1H), 2.50–2.18(m, 7H), 2.04–1.65(m, 9H), 1.40(s, 3H, CH$_3$-15), 1.31(s, 3H), 1.28(s, 3H), 1.22–1.15(m, 2H), 0.96(d, 3H, J=5.8 Hz, CH$_3$-13), 0.88(d, 3H, J=7.5 Hz, CH$_3$-14), 0.85(m, 1H).

$^{13}$C-NMR (CDCl$_3$, 63 MHz) δ173.2, 172.3, 103.7, 89.1, 81.5, 76.8, 76.3, 61.9, 61.0, 52.7, 52.0, 44.8, 37.7, 36.8, 34.8, 34.8, 31.2, 30.7, 30.5, 27.8, 26.4, 25.2, 25.0, 20.5, 14.5, 13.5.

IR(neat) u$_{max}$ 3370(NH), 2939, 2878, 1737(C=O), 1669 (C=O), 1533, 1446, 1372, 1054, 1012, 880(O—O), 742 cm$^{-1}$ MS(FAB) m/z 526.5([M+H]$^+$).

Elemental analysis (C$_{27}$H$_{43}$NO$_9$) C, H, N.

(2) Synthesis of N-[12-(3-deoxoartemisinin)propionyl]-L-glutamic diacid (XII)

N-[12-(β-deoxoartemisinin)propionyl]-L-glutamic diethylester (XI) (2 mg, 0.08 mmol) was dissolved in TBF/H$_2$O (1/1, 5 mL), 1N LiOH (1 mL) was added and then was allowed to stir at room temperature for 2 hours. To the reaction mixture was added 1N HCl (1 mL). The resulting reaction mixture was extracted with ethyl acetate (20 mL×3)

and washed with brine (10 mL×2). The extract was dried over MgSO$_4$, concentrated in vacuo, then purified by silica gel column (hexane/ethyl acetate=1/2 as eluent) to afford N-[12-(β-deoxoartemisinin)propionyl]-L-glutamic diacid (XII) (30.8 mg, 82%) as a colorless oil.

$[\alpha]^{26}{}_D$=+76.8 (c 0.22, CHCl$_3$).

m.p. 106° C.

$^1$H-NMR (CDCl$_3$, 250 MHz) δ8.96(br, 2H, CO$_2$H), 7.08 (d, 1H, 3=6.5 Hz, NH), 5.34(s, 1H, H-5), 4.62–4.60(m, 1H), 4.12–4.04(m, 1H, H-12), 2.72–2.70(m, 1H), 2.48–2.26(m, 6H), 2.08–1.98(m, 3H), 1.82–1.78(m, 3H), 1.71–1.42(m, 4H), 1.41(s, 3H, CH$_3$-14), 1.27–1.21(m, 2H), 0.95(d, 3H, J=5.3 Hz, CH$_3$-13), 0.87(d, 3H, J=7.2 Hz, CH$_3$-14), 0.84(m, 1H).

$^{13}$C-NMR (CDCl$_3$, 63 MHz) δ177.3, 176.6, 175.1, 174.7, 104.3, 89.0, 81.5, 76.9, 52.8, 52.1, 44.9, 37.6 36.8, 34.8, 34.5, 30.4, 27.1, 26.2, 25.1, 24.9, 21.0, 20.6, 13.7.

IR(KBr) u$_{max}$ 3346(CO$_2$H), 2942, 2877, 1728(C=O), 1631(C=O), 1539, 1453, 1381, 1202, 1051, 912, 880(O—O), 732 cm$^{-1}$ LCMS(ESI) m/z 492 ([M+Na]$^+$).

Elemental analysis (C$_{23}$H$_{35}$NO$_9$) C, H, N.

(3) Synthesis of the Title Compound

N-[12-(β-deoxoartemisinin)propionyl]-L-glutamic diacid (XII) (22 mg, 0.047 mmol) was dissolved in dry CH$_2$Cl$_2$ (2 mL) and HOBt (27 mg, 0.141 mmol) and EDC (31 mg, 0.141 mmol) were added. The reaction mixture was allowed to stir at room temperature for 30 minutes and 12-(2'-aminoethyl)deoxoartemisinin (VI) (29 mg, 0.093 mmol) was added. The resulting reaction mixture was allowed to stir at room temperature for 19 hours. The reaction mixture was extracted with ethyl acetate (30 mL×3) and washed with brine (20 mL×2). The extract was dried over MgSO$_4$, concentrated in vacuo, then purified by silica gel column (hexane/ethyl acetate=1/2 as eluent) to afford deoxoartemisinin trimer (IVe) (73.3 mg, 74%) as a colorless solid.

$[\alpha]^{24}{}_D$=+102.7 (c 0.41, CHCl$_3$).

m.p. 138° C.

$^1$H-NMR (CDCl$_3$, 250 MHz) δ7.13–7.04(m, 2H, NH), 6.83–6.81(m, 1H, NH), 5.32(s, 2H, H-5), 5.29(s, 1H, H-5), 4.39–4.34(m, 3H, H-12), 4.29–4.26(m, 1H), 3.55–3.48(m, 2H), 3.32–3.27(m, 2H), 2.65–2.63(m, 3H), 2.36–2.31(m, 7H), 2.17–1.93(m, 11H), 1.91–1.51(m, 17H), 1.39(s, 9H, CH$_3$-15), 1.33–1.21(m, 7H), 0.95(d, 9H, J=5.4 Hz, CH$_3$-13), 0.88–0.83(m, 9H, CH$_3$-14), 0.82(m, 3H).

$^{13}$C-NMR (CDCl$_3$, 63 MHz) δ174.4, 174.3, 173.2, 173.1, 103.5, 103.4, 89.9, 89.8, 81.5, 81.4, 76.8, 53.2, 53.1, 52.8, 52.6, 52.4, 37.7, 36.8, 34.7, 31.3, 30.8, 30.7, 30.0, 29.1, 26.4, 26.4, 25.1, 20.5, 20.4, 13.2, 13.1.

IR (KBr) u$_{max}$ 3308(NH), 2933, 2875, 1667(C=O), 1535, 1465, 1377, 1102, 1061, 1014, 938, 874(O—O), 751 cm$^{-1}$ HRMS (FAB) m/z 1056.6392([M+H]$^+$, obsd), 1055.6294 (calcd for C$_{57}$H$_{89}$N$_3$O$_{15}$).

Elemental analysis (C$_{57}$H$_{89}$N$_3$O$_{15}$) C, H, N.

Example 10

Synthesis of 12-(4'-aminobutyl)deoxoartemisinin (VI')

(1) Synthesis of 12-(4'-butyl azide)deoxoartemisinin 12-(4'-butyl azide)deoxoartemisinin (116.9 mg, 92%) was prepared as a colorless oil by following the procedure of Example 2 (1), but replacing 12-(2'-bromoethyl)deoxoartemisinin with 12-(4'-bromobutyl)deoxoartemisinin (137.9 mg, 0.352 mmol).

$[\alpha]^{24}{}_D$=+71.3 (c 0.1, CHCl$_3$).

$^1$H-NMR (CDCl$_3$, 250 MHz) δ5.29(s, 1H, H-5), 4.19–4.12(m, 1H, H-12), 3.26(t, 2H, J=6.6 Hz, H-4), 2.64–2.62(m, 1H), 2.31(ddd, 1H, J=4.1, 3.8, 4.1 Hz), 2.04–1.89(m, 2H), 1.68–1.65(m, 2H), 1.63–1.58(m, 7H), 1.40(s, 3H, CH$_3$-15), 1.34–1.22(m, 2H), J=5.7 Hz, CH$_3$-13), 0.86(d, 3H, J=7.5 Hz), 0.82(m, 1H).

$^{13}$C-NMR (CDCl$_3$, 63 MHz), δ103.4, 89.4, 81.4, 75.3, 52.6, 51.7, 44.6, 37.7, 36.9, 34.7, 30.6, 29.3, 29.0, 26.4, 25.2, 25.0, 25.0, 20.5, 13.2.

IR (neat) u$_{max}$ 2927, 2876, 2095(N$_3$), 1597, 1454, 1379, 1255, 1097, 1012, 946, 881(O—O), 643 cm$^{-1}$

MS (FAB) 366.4([M+H]$^+$).

(2) Synthesis of the Title Compound 12-(4'-aminobutyl)deoxoartemisinin (VI') (94.3 mg, 79%) was prepared as a white solid by following the procedure of Example 2 (2), but replacing 12-(2'-ethyl azide)deoxoartemisinin with 12-(4'-butyl azide)deoxoartemisinin (128.8 mg, 0.352 mmol).

$[\alpha]^{25}{}_D$=+49.4 (c 0.1, CHCl$_3$).

m.p. 105° C.

$^1$H-NMR (CDCl$_3$, 250 MHz) δ5.29(s, 1H, H-5), 4.16–4.09(m, 1H, H-12), 2.71–2.66(m, 3H), 2.32(ddd, 1H, J=4.1, 3.8, 4.1 Hz), 2.08–2.04(m, 2H), 1.87–1.72(m, 3H), 1.66–1.53(m, 4H), 1.51–1.45(m, 4H), 1.41(s, 3H, CH$_3$-15), 1.36–1.24(m, 4H), 0.96(d, 3H, J=4.3 Hz), 0.86(d, 3H, J=7.5 Hz), 0.83(m, 1H).

$^{13}$C-NMR (CDCl$_3$, 63 MHz), δ103.5, 89.4, 81.5, 76.0, 52.6, 51.8, 44.8, 38.4, 36.9, 34.8, 31.2, 29.4, 29.0, 26.5, 25.3, 25.2, 25.1, 20.5, 13.3.

IR(KBr) u$_{max}$ 3378(NH), 2925, 1591, 1454, 1379, 1117, 1038, 1005, 887(O—O), 748 cm$^{-1}$ HRMS(FAB) m/z 340.2402([M+H]$^+$, obsd), 339.2410 (calcd for C$_{19}$H$_{33}$NO$_4$).

Elemental analysis (C$_{19}$H$_{33}$NO$_4$) C, H, N.

Example 11

Synthesis of 12-(4'-aminobutyl)deoxoartemisinin dimer (IVc')

12-(4'-aminobutyl)deoxoartemisinin dimer (IVc') (46 mg, 81%) was prepared as a colorless oil by following the procedure of Example 7, but replacing 12-(2'-aminoethyl) deoxoartemisinin with 12-(4'-aminobutyl)deoxoartemisinin (28 mg, 0.096 mmol).

$[\alpha]^{23}{}_D$=+104.2 (c 0.23, CHCl$_3$).

$^1$H-NMR (CDCl$_3$, 250 MHz) δ5.68(s, 1H, NH), 5.28(s, 2H, H-5), 4.13–4.03(m, 2H, H-12), 3.25–3.21(m, 2H, H-4), 2.72–2.65(m, 2H), 2.39–2.21(m, 4H), 2.11–1.67(m, 9H), 1.61–1.46(m, 10H), 1.40(s, 6H, CH$_3$-15), 1.36–1.22(m, 7H), 0.96(d, 6H, J=4.6 Hz, CH$_3$-13), 0.89(d, 3H, J=7.4 Hz, CH$_3$-14), 0.86(d, 3H, J=7.4 Hz, CH$_3$-14), 0.83(m, 2H).

$^{13}$C-NMR (CDCl$_3$, 63 MHz) δ173.3, 126.5, 126.3, 118.2, 112.5, 103.7, 103.6, 89.4, 89.1, 81.5, 76.9, 76.4, 75.9, 52.8, 52.5, 44.8, 44.3, 37.8, 37.0, 36.4, 36.1, 35.2, 35.1, 34.8, 34.3, 30.6, 30.6, 26.6, 26.4, 25.2, 25.1, 25.1, 25.1, 20.6, 20.5, 13.7, 13.6.

IR(neat) $u_{max}$ 3388(NH), 2936, 2875, 1650(C=O), 1539, 1452(C—N), 1379, 1216, 1097, 1051, 1005, 873(O—O), 753 cm$^{-1}$ HRMS(FAB) m/z 662.4173([M+H]$^+$, obsd), 661.4190 (calcd for $C_{37}H_{59}NO_9$).

Elemental analysis ($C_{37}H_{59}NO_9$) C, H, N.

Example 12

Measurement of Anticancer Activity

The anticancer activities of the deoxoartemisinin dimer and trimer of the present invention were measured by a known micro-culture tetrazolium assay (see Carmichel, J.; DeGraff, W. G; Gazdar, A. F.; Minna, J. D.; Mitchell, J. B., Evaluation of a Tetrazolium-based Semiautomated Colorimetric Assay: Assessment of Chemosensitivity testing, *Cancer Res.*, 1987, 47, 936–42).

The table 1 shows cytotoxicities of the compounds of the present invention on mouse and human cancer cells in vitro.

TABLE 1

| | In vitro cytotoxicities ($IC_{50}$ (μg/mL)) | | | | | | | |
|---|---|---|---|---|---|---|---|---|
| | P388 | EL4 | Bewo | HT-29 | PANC-1 | SKOV3 | MCF7 | A549 |
| Compound (IVa$_1$) | 0.40 | 0.23 | 14.20 | 0.24 | | | 0.017 | |
| Compound (IVa$_2$) | 5.60 | 0.54 | 1.04 | 0.38 | | | 0.025 | |
| Compound (IVb) | 8.40 | 10.00 | 8.50 | 0.38 | | | 5.6 | |
| Compound (IVc) | 10.40 | 6.29 | 7.50 | 0.69 | | 12.6 | 0.005 | |
| Compound (IVc') | >20 | >20 | >20 | 20.20 | | | >20 | |
| Compound (IVd) | 15.60 | 16.50 | >20 | 6.50 | | | 15.3 | |
| Compound (IVe) | 0.12 | 1.07 | 18.30 | 0.09 | 2.69 | 11.2 | 0.017 | 2.45 |
| Adriamycin | 0.39 | 0.67 | 6.24 | 0.10 | | | 0.12 | |
| Mitomycin | 1.50 | 3.94 | 0.85 | 0.02 | | | 0.93 | 1.85 |
| Taxol | 2.27 | 1.34 | 7.39 | 0.01 | 5.76 | 12.30 | 0.0001 | |

P388: mouse fibroblast leukemia cell
EL4: mouse thymoma cell
Bewo: human choriocarcinoma cell
HT-29: human colorectal adenocarcinoma cell
PANC-1: human pancreatic cancer cell
SKOV3: human ovarian carcinoma cell
MCF7: human breast carcinoma cell
A549: human lung cancer cell As shown in Table 1, the sulfide dimer (IVa$_1$) of the present invention exhibited an anticancer activity on the mouse fibroblast leukemia cell (P388), said activity being comparable to that of adriamycin and being at least 4-fold higher than that of mitomycin. Also, the trimer (IVe) of the present invention exhibited an anticancer activity on P388, said activity being at least 3-fold higher than that of adrimycin, at least 12-fold higher than that of mitomycin and at least 20-fold higher than that of taxol. The sulfide dimer (IVa$_1$), sulfone dimer (IVa$_2$) and trimer (IVe) of the present invention exhibited an anticancer activity on the mouse thymoma cell (EL4), said activity being comparable to that of adriamycin. Most compounds had little anticancer activity on human choriocarcinoma cell (Bewo) but the sulfone dimer (IVa$_2$) had an anticancer activity on Bewo, which was comparable to that of mitomycin and was at least 6-fold higher than that of taxol and adriamycin. The trimer (IVe) of the present invention exhibited an anticancer activity on human colorectal adenocarcinoma cell (HT-29), said activity being comparable to that of adriamycin, and also exhibited an anticancer activity on human pancreatic cancer cell, said activity being at least 2-fold higher than that of taxol. Most compounds had little anticancer activity on human ovarian carcinoma cell (SKOV3), while the amide dimer (IVc) and trimer (Ive) of the present invention had an anticancer activity similar to that of taxol. The amide dimer (IVc), sulfide dimer (IVa$_1$), sulfone dimer (IVa$_2$) and trimer (IVe) had higher anticancer activity on human breast carcinoma cell (MCF7). Especially, the amide dimer (IVc) of the present invention exhibited an anticancer activity on MCF7, said activity being at least 24-fold higher than that of adriamycin and at least 200-fold higher than that of mitomycin. Most of the compounds had less anticancer activity on human lung cancer cell (A549), while the trimer (IVe) of the present invention had an anticancer activity on A549 similar to that of mitomycin.

From the results, it can be seen that the trimer (IVe) of the present invention has a very excellent anticancer activity on most mouse and human cancer cells. Also, it can be seen that the anticancer activity of the dimer of the present invention depends on the length of the linker located between two deoxoartemisinins. In other words, the compounds (IVa$_1$), (IVa$_2$) and (IVc), in which a linker has one amide- or one sulfur-centered two ethylene groups, have superior anticancer activity to the compounds (IVa$_1$), (IVa$_2$) and (IVc), in which a linker is longer than the length of two ethylene groups.

INDUSTRIAL APPLICABILITY

The deoxoartemisinin dimer and trimer of the present invention are C-12 non-acetal-type and do not have linker containing C—O bonds, aromatic or unsaturated groups at C-12 positions, and thus are acid stable, less toxic and have higher anticancer activity.

Also, according to the preparation of the present invention, the deoxoartemisinin analog is easily prepared in high yield.

The invention claimed is:

1. A deoxoartemisinin compound of the

[chemical structure of dimeric deoxoartemisinin with linker Y]

—S—, —SO$_2$—,

[structures showing $\underset{(O)_2}{S}$ propyl $S$ and $\underset{(O)_2}{S}$ propyl $\underset{(O)_2}{S}$ linkers]

wherein Y is

[structures of Y linkers including amide and glutamic-acid-based linkers] or

[chemical structure of deoxoartemisinin monomer with glutamic amide substituent]

2. A method for preparing deoxoartemisinin trimer of the following formula, said method comprising the steps of:
   (a) coupling 12-carboxylethyldeoxoartemisinin with L-glutamic diethylester;
   (b) hydrolyzing two ester groups of the product from said step (a); and
   (c) doubly coupling the product from said step (b) with 2 moles of 12-aminoethyldeoxoartemisinin:

[chemical structure of deoxoartemisinin trimer]

3. The method as claimed in claim 2, wherein said coupling reaction is carried in the presence of 1-ethyl-3-(3-dimethylaminopropyl)carbodiimide and 10-hydroxybenzotriazole (EDC/HOBt).

4. A method for preparing of the following formula, said method comprising the steps of:
   (a) hydroborative oxidizing a terminal olefin of 12-vinyldihydroartemisinyl alcohol;
   (b) brominating the product from said step (a) with CBr$_4$/PPh$_3$;
   (c) photooxygenative cyclizing the product from said step (b);
   (d) reacting the product from said step (c) with sodium azide; and
   (e) reducing an azide group of the product from said step (d):

[chemical structure of 12-aminoethyldeoxoartemisinin]

* * * * *